United States Patent [19]

Levy et al.

[11] 3,966,831
[45] June 29, 1976

[54] PRODUCTION OF BROMOSTYRENES

[75] Inventors: Moshe Levy; David Vofsi; Stephen Daren, all of Rehovot; Ella Cohen, Ramat-Hasharon, all of Israel

[73] Assignee: Yeda Research & Development Co. Ltd., Rehovot, Israel

[22] Filed: Feb. 7, 1975

[21] Appl. No.: 547,861

Related U.S. Application Data

[63] Continuation-in-part of Ser. No. 376,171, July 3, 1973.

[30] Foreign Application Priority Data

July 26, 1974 Israel.................................... 45356

[52] U.S. Cl............................................ 260/650 R
[51] Int. Cl.².......................................... C07C 25/28
[58] Field of Search......................... 260/650 R, 657

[56] References Cited

UNITED STATES PATENTS

| | | | |
|---|---|---|---|
| 3,737,469 | 6/1973 | Berger et al. | 260/650 R |
| 3,867,468 | 2/1975 | Vofsi et al. | 260/650 R |

*Primary Examiner*—D. Horwitz
*Attorney, Agent, or Firm*—Hubbell, Cohen, Stiefel & Gross

[57] ABSTRACT

A process for the production of mono-, di-, and/or tribromostyrene which comprises reacting β-bromo-methyl-mono-, di- and/or tribromobenzene at a temperature between 280°C to 470°C in the presence of a free radical source and either a lower alkanol or water.

7 Claims, No Drawings

PRODUCTION OF BROMOSTYRENES

CROSS-REFERENCE TO RELATED APPLICATIONS

This is a continuation-in-part of our copending application Ser. No. 376,171, filed July 3, 1973.

BACKGROUND OF THE INVENTION

A known process for the production of bromostyrene comprises effecting dehydration of the respective bromophenyl methyl carbinol, or the respective bromophenyl ethyl alcohol. Another known process, exemplified in British Pat. No. 986,634, involves the dehydrobromination of either of the respective α or β haloethyl mono-bromobenzene isomers.

The dehydrobromination of bromoethyl halobenzenes is effected by passing a mixture of the reactants together with an excess of steam over granular calcium sulfate catalyst. The use of calcium sulfate as a catalyst is also mentioned in U.S. Pat. No. 2,485,524 in vapor-phase dehydrohalogenations of substituted halo-benzenes. Other catalysts mentioned in the literature for dehydrohalogenations are calcium chloride, calcium oxide, calcium phosphate and various aluminas.

When applied to bromoethyl bromobenzene, all of these catalysts exhibit the serious disadvantage of causing the formation and deposition on the catalyst, of tarry substances, most probably comprising a polymer formed from the monomeric bromostyrene which is the primary product of the catalytic dehydrohalogenation. The formation of the polymer cannot be avoided, even when a large excess of an inert diluent, such as steam or nitrogen, is fed, together with the substrate into the reaction zone. The deposition of the polymer on the catalyst rapidly reduces its activity and thus frequent catalyst regenerations are required. If, to avoid this problem, the catalyst is discarded after relatively brief runs, the recharging with fresh catalyst makes the process comparatively expensive.

To eliminate the deposition of the tarry byproducts on the fixed bed of catalyst, a process is described in French Pat. No. 1,576,909, wherein the active catalyst as well as the reaction medium comprises certain mixtures of molten salts, and in particular mixtures containing bivalent metal chlorides, such as copper chloride, in combination with other salts which decrease the melting point of the salt mixture.

According to the above disclosure, it is possible to obtain, for example, high yields of vinyl chloride by the elimination of hydrogen chloride from ethylene dichloride; however, the said process produces only poor yields of monomers in the case of heavy, relatively non-volatile substrates. In particular, when the substrates according to the present invention are used, the conversion to the respective products is far from complete.

In U.S. Pat. No. 3,737,469 a process is described whereby molten salts are used very effectively as a reaction medium for the production of bromostyrene by passing through this medium the said substrate together with an aliphatic alcohol, and in particular methyl alcohol. The alcohol acts as an acceptor, or scavanger for the hydrogen halide which is eliminated from the substrate during the reaction.

It is believed that the fast reaction of the alcohol with the eliminated hydrogen halide has a pronounced beneficial effect on the yield of the desired product. The process can thus also be carried out at temperatures that are substantially lower than in the absence of the alcohol. This has the effect of increasing the selectivity of the reaction with respect to the desired product.

While results according to U.S. Pat. No. 3,737,469 are generally satisfactory, said process has certain insufficiencies, such as, for the need for special materials of construction to be used for the reactors containing highly corrosive molten salts. Another disadvantage of said process is in the high ratio of reactor-space to product produced per unit time (low space-time yields).

A further disadvantage is the formation of small quantities of saturated products such as ethyl bromobenzenes. These products have boiling points very close to that of bromostyrene, and it is therefore very difficult to separate them by fractional distillation. These saturated impurities are not polymerizable and act as chain transfer agents, thus interfering in the high molecular weight polymerization of the bromostyrenes.

SUMMARY OF THE INVENTION

The present invention relates to a process for the production of monobromostyrene, dibromostyrene and/or tribromostyrene by reacting β-bromoethyl monobromobenzene, β-bromoethyl dibromobenzene or β-bromoethyl tribromobenzene, respectively, in the presence of a free radical source, and either a lower alkanol or water, in the vapor phase at an elevated temperature. With the free radical catalyst the reaction proceeds satisfactorily even at temperatures as low as 280°C.

Any suitable source of free radicals can be used, e.g. peroxides and hydroperoxides such as di-t-butyl peroxides, dicumyl peroxide, benzoyl peroxide, t-butyl hydroperoxide, hydrogen peroxide (dry or in water solution) or other decomposable species such as azobis-isobutyronitrile, lead tetraethyl or bromine. However, the organic peroxides are preferred, particularly the dialkyl peroxides such as di-tert-butyl peroxide.

The free radical source should be present in an amount of from 0.3 to 5% based on the weight of the reaction mixture.

By using a free radical catalyst, the temperature of the reaction can be decreased considerably, to as low as 280°C, with the concomitant saving in power. Furthermore, smaller reactors can be used as the reaction contact time is shorter.

Another advantage of the pyrolytic method according to this invention is that the reaction tube can be cleaned readily of any tars formed during the pyrolysis by simply passing air through the hot reactor and burning them, since there is no packing or catalyst in the reactor.

The primary advantage of this invention, though, is the accelerated reaction rate with simultaneous elimination or reduction of side reactions, thus providing purer monomer at a faster rate.

Bromostyrene is a reactive monomer which can be polymerized to a hard, transparent plastic which has many uses. It can be copolymerized with other monomers to form copolymers which are fire retardant and self-extinguishing. It is of particular interest as a reactive component in unsaturated polyester compositions, to result in self-extinguishing transparent plastic compositions which do not become discolored upon prolonged exposure to weather conditions.

3

The term "bromostyrene" as used herein means para-bromo, metabromo, or ortho-bromo-styrene or a mixture of any of these.

Whereas the purification of bromostyrene and especially of dibromostyrene presents some problems when carried out on a larger scale, the tribromostyrene which is obtained according to one of the embodiments of the present invention can be purified in a very convenient manner by crystallization. Due to its high specific content of bromine, tribromostyrene is a very valuable component for the production of fire-retardant polymers.

DESCRIPTION OF THE PREFERRED EMBODIMENTS

The following examples are intended to be illustrative, and are not to be construed in a limitative manner.

EXAMPLE 1

A quantity of 2 g of di-tertbutyl peroxide was dissolved in 100g of β-bromoethyl bromobenzene and the solution was added through a motor-driven syringe into the reactor at a rate of 60g/h, together with 25 g of methanol and with nitrogen which was passed in at a rate of 2 l/h. The reactor used in this example was a glass spiral made of 6 mm wide and 5 m long tube heated to 300°–320°C. The products were collected in a trap immersed in an ice bath while the methyl bromide was trapped in a container positioned in liquid nitrogen. The liquid products were then subjected to fractional distillation under vacuum. There were obtained 58 g bromostyrene and 12 g unconverted reactant. The yield was 95% bromostyrene.

EXAMPLE 2

A quantity of 170 g of β-bromoethyl dibromobenzene(approximately 1:1 ratio of 2,4- to 3,4-isomers) containing 4 g of di-butyl peroxide was injected into the reactor together with methanol at rates of 20 g/h and 4.4 g/h respectively. The reactor was kept at 340°–360°C. After distillation, a crop of 20 g of unconverted reactants and 103 g. of dibromostyrene were obtained (90% yield of dibromostyrene).

EXAMPLE 3

1.2 g of di-tert-butyl peroxide were dissolved in 60 g of β-bromoethyl bromobenzene. The mixture (70 g/h) was introduced into a spiral glass tube reactor 6 mm wide and 5.5 mm long together with methanol (15 g/h). The temperature of the reactor was maintained at 345°C. The liquid products after fractional distillation contained 7 g of β-bromoethyl bromobenzene and 35 g of bromostyrene, corresponding to 88% conversion and 94% yield. The bromostyrene fraction was free of ethyl bromobenzene.

EXAMPLE 4

2 g. of tert-butyl hydroperoxide were dissolved in 100 g of β-bromoethyl bromobenzene and the mixture, together with methanol was introduced into a spiral glass reactor 8 mm wide and 100 mm long packed with graphite. The rates of flow were 100 g/h and 24 g/h respectively. The temperature of the reactor was maintained at 340°C. Bromostyrene was recovered from the liquid reaction product with a conversion of 80%.

EXAMPLE 5

2 g of di-tert-butyl peroxide were dissolved in 100 g of β-bromoethyl bromobenzene and introduced into glass spiral reactors (6mm diameter) of varying lengths at 100 g/h with methanol (22 g/h) at 320°C. The results were as follows:

| Reactor Length (meters) | Conversion to Bromostyrene |
| --- | --- |
| 5.5 | 91% |
| 2.8 | 90% |
| 1.4 | 90% |
| 0.3 | 80% |

Thus, using a peroxide initiator, the reactor size can be reduced by a factor of 4 or 5 without affecting the conversion to bromostyrene. When, instead of using a 6mm diameter tube 2.8mm long, a 4mm tube 2.8mm long was used as the reactor, the conversion to bromostyrene increased to 96%, presumably due to improved heat exchange.

EXAMPLE 6

70 g of β-bromoethyl bromobenzene and superheated steam were simultaneously introduced into a reactor as described in Example 1, at a temperature of 360°C for 1 hour. The liquid product was recovered with a conversion to bromostyrene of 30%.

EXAMPLE 7

2 g of di-tert-butyl peroxide were dissolved in 100 g of β-bromoethyl bromobenzene and fed into the reactor described in Example 1 at a rate of 70 g/h together with superheated steam (20 g/h). The temperature of the reaction was maintained at 360°C. The products yielded bromostyrene at a conversion of 90%.

EXAMPLES OF PRODUCTION OF TRIBROMOSTYRENE

EXAMPLE 8

37 g of beta-bromoethyl-tribromobenzene (mainly the 2,4,5-isomer) containing 1% (w/w) of ditertiary butyl peroxide (15 ml/h) and methanol (15 ml/h) were introduced into a glass spiral reactor (2.8 m. × 5 mm.) at 470°C. Nitrogen (2 l/h) was used as a carrier.

The liquid products were collected in a stirred mixture of methylene chloride and water while the methyl bromide was collected in a liquid air trap. When the reaction was completed, the methylene chloride layer was separated from the water layer in a separating funnel and dried over calcium chloride. Gas chromatographic analysis at this stage indicated 85% conversion to tribromostyrene.

The dry methylene chloride solution was filtered to remove the calcium chloride and then dry methanol was added to it until the solution became cloudy. The cloudy solution was filtered to remove heavy (polymeric) materials (0.1 g) and then an excess of methanol was added until the solution was once more cloudy. The solution was concentrated by evaporation under vacuum at room temperature until an oily precipitate started to appear. The oily precipitate was redissolved by the addition of a few drops of methylene chloride and the solution was placed in an ice-box at −10°C. White crystals of tribromostyrene (20 g) (m.p. 66°C) corresponding to a yield of 79% were obtained.

EXAMPLE 9

47 g of β-bromoethyl tribromobenzene containing 1% w/w of ditertiary butyl peroxide (45 ml/h) and methanol (45 ml/h) were introduced into a glass spiral reactor at 470°C as described in Example 8.

The products were worked-up as described in Example 8 and gas-chromatographic analysis indicated 70% conversion to tribromostyrene. On crystallization, 25 g of tribromostyrene, corresponding to a 94% yield were obtained.

We claim:

1. A process for the production of a compound selected from the group consisting of monobromostyrene, dibromostyrene and tribromostyrene, said process comprising reacting β-bromoethyl-monobromobenzene, β-bromoethyl-dibromobenzene and β-bromoethyl-tribromobenzene, respectively, with a lower alkanol or water, at a temperature between 280°C. and 470°C. in the presence of a chemical source of free radicals.

2. A process according to claim 1, wherein the chemical source of free radicals in an organic peroxide.

3. A process according to claim 2, wherein the organic peroxide is di-t-butyl peroxide.

4. A process according to claim 1, wherein the reaction is effected in the presence of an inert carrier gas.

5. A process according to claim 1, wherein the lower alkanol is methanol.

6. A process according to claim 1, wherein the chemical source of free radicals is used in a quantity of from 0.3% to 5.0% by weight based on the total weight of the reaction mixture.

7. A process according to claim 1, wherein the chemical source of free radicals is selected from the group consisting of organic peroxides, organic hydroperoxides, hydrogen peroxide, azobisisobutyronitrile, lead tetraethyl and bromine.

* * * * *

UNITED STATES PATENT OFFICE
CERTIFICATE OF CORRECTION

Patent No. 3,966,831         Dated June 29, 1976

Inventor(s) MOSHE LEVY et al

It is certified that error appears in the above-identified patent and that said Letters Patent are hereby corrected as shown below:

Title page, right side, lines 2-3 of the Abstract: "β-bromomethyl-mono-," should read -- β-bromoethyl-mono-, --.

Column 2, line 7: "such as, for" should read -- such as --.

Column 6, line 2 of claim 2: "in an" should read -- is an --.

Signed and Sealed this

Fourteenth Day of September 1976

[SEAL]

Attest:

RUTH C. MASON
Attesting Officer

C. MARSHALL DANN
Commissioner of Patents and Trademarks